(12) United States Patent
Moore et al.

(10) Patent No.: US 11,666,568 B2
(45) Date of Patent: Jun. 6, 2023

(54) PHARMACEUTICAL COMBINATIONS COMPRISING A HISTONE DEACETYLASE INHIBITOR AND A BCL-2 INHIBITOR AND METHODS OF USE THEREOF

(71) Applicant: ACETYLON PHARMACEUTICALS, INC., Boston, MA (US)

(72) Inventors: Nathan Moore, Providence, RI (US); Chengyin Min, Wellesley, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 208 days.

(21) Appl. No.: 16/344,873

(22) PCT Filed: Nov. 3, 2017

(86) PCT No.: PCT/US2017/059927
§ 371 (c)(1),
(2) Date: Apr. 25, 2019

(87) PCT Pub. No.: WO2018/085652
PCT Pub. Date: May 11, 2018

(65) Prior Publication Data
US 2019/0262337 A1 Aug. 29, 2019

Related U.S. Application Data

(60) Provisional application No. 62/417,670, filed on Nov. 4, 2016.

(51) Int. Cl.
*A61K 31/505* (2006.01)
*A61P 35/02* (2006.01)
*A61K 31/635* (2006.01)
*C07D 239/42* (2006.01)

(52) U.S. Cl.
CPC .......... *A61K 31/505* (2013.01); *A61K 31/635* (2013.01); *A61P 35/02* (2018.01); *C07D 239/42* (2013.01)

(58) Field of Classification Search
None
See application file for complete search history.

(56) References Cited

U.S. PATENT DOCUMENTS

| 8,394,810 | B2 * | 3/2013 | van Duzer | A61P 1/00 514/275 |
|---|---|---|---|---|
| 2010/0311751 | A1 | 12/2010 | Schmitt et al. | |
| 2011/0300134 | A1 * | 12/2011 | van Duzer | |
| 2015/0150871 | A1 | 6/2015 | Quayle et al. | |

FOREIGN PATENT DOCUMENTS

| WO | WO 2010/144464 A2 | 12/2010 |
| WO | WO 2011/091213 A2 | 7/2011 |
| WO | WO-2011091213 A2 * | 7/2011 |
| WO | WO 2015/171591 A1 | 11/2015 |
| WO | WO 2015/171591 A1 * | 12/2015 |

OTHER PUBLICATIONS

Medicinenet, "Medical Definition of Cancer", https://www.medicinenet.com/cancer/definition.htm, 1 page; downloaded on Mar. 23, 2021.*
Touzeau et al., "The Bcl-2 specific BH3 mimetic ABT-199: a promising targeted therapy for t(11;14) multiple myeloma", Leukemia 28, 210-212 (2014). (Year: 2014).*
NCI Dictionary of Cancer Terms, "Definition of hematologic cancer", National Cancer Institute, retrieved on Jan. 13, 2022 from URL < www.cancer.gov/publications/dictionaries/cancer-terms/def/hematologic-cancer>, 1 page. (Year: 2022).*
Adams et al., "The BCL-2 protein family: arbiters of cell survival", Science, 1998, 281: 1322-1326.
Benito et al., "MLL-Rearranged Acute Lymphoblastic Leukemias Activate BLC-2 through H3K79 Methylation and Are Sensitive to the BCL-2-Specific Antagonist ABT-199", Cell Reports, 2015, 13(12): 2715-2727.
Chou et al., "Quantitative Analysis of Dose-Effect Relationships: The Combined Effects of Multiple Drugs or Enzyme Inhibitors", Adv. Enzyme Regul., 1984, 22: 27-55.
clinicaltrials.gov, NCT02920697, "Dose-escalation Study of Oral Administration of S 55746 in Patients With Chronic Lymphocytic Leukaemia and B-Cell Non-Hodgkin Lymphoma", Sep. 30, 2016, obtained from url: https://clinicaltrials.gov/ct2/show/NCT02920697, 8 pages.
Danial et al., "Cell death: critical control points", Cell, 2004, 116: 205-219.
Extended European Search Report for European Patent Application No. 17866600.4, dated May 2, 2020, 9 pages.
FDA Label for Venclexta™, obtained from url: https://www.accessdata.fda.gov/drugsatfda_docs/label/2016/208573s000lbl.pdf, 25 pages.
Holford et al., "Understanding the Dose-Effect Relationship: Clinical Application of Pharmacokinetic-Pharmacodynamic Models", Clin. Pharmacokinet., 1981, 6: 429-453.
International Search Report and Written Opinion for PCT International Patent Application No. PCT/US2017/059927, dated Jan. 11, 2018, 9 pages.
Loewe et al., "Über Kombinationswirkungen", Arch. Exp. Pathol. Pharmacol., 1926, 114: 313-326.
Puvvada et al. "Emerging Frontiers in Therapeutics of Diffuse Large B Cell Lymphoma: Epigenetics and B Cell Receptor Signaling", Journal of Cancer Therapy, 2013, 4: 485-491.

* cited by examiner

*Primary Examiner* — Savitha M Rao
*Assistant Examiner* — Gregg Polansky
(74) *Attorney, Agent, or Firm* — Brian C. Trinque; Lathrop GPM LLP

(57) ABSTRACT

The present disclosure relates to a pharmaceutical combination comprising (a) a histone deacetylase 6 inhibitor and (b) a BCL-2 inhibitor, including combined preparations and pharmaceutical compositions thereof; uses of such combination in the treatment or prevention of cancer; and methods of treating or preventing cancer in a subject comprising administering a therapeutically effective amount of such combination.

6 Claims, 5 Drawing Sheets

PHARMACEUTICAL COMBINATIONS COMPRISING A HISTONE DEACETYLASE INHIBITOR AND A BCL-2 INHIBITOR AND METHODS OF USE THEREOF

CROSS-REFERENCE TO RELATED APPLICATIONS

This application is a 35 U.S.C. § 371 filing of International Application No. PCT/US/2017/059927, filed Nov. 3, 2017, which application claims the benefit of U.S. Provisional Application No. 62/417,670, filed Nov. 4, 2016, the contents of which are incorporated herein by reference in their entireties.

BACKGROUND

Histone deacetylase (H DAC) inhibition can cause cancer cell growth arrest. However, pan-HDAC inhibition leads to significant adverse effects, and an alternative HDAC inhibition profile is desirable.

HDAC6 is a class IIb HDAC and is known to remove acetyl groups from many cellular proteins, including a-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

In spite of numerous treatment options for cancer patients, there remains a need for effective and safe therapeutic options. In particular, there is a need for effective methods of treating or preventing cancers, especially those cancers that have been resistant and/or refractive to current therapies. This need can be fulfilled by the use of combination therapies such as those described herein.

SUMMARY

Provided herein is a pharmaceutical combination comprising a histone deacetylase inhibitor 6 (referred to herein as "HDAC6") inhibitor and a B-cell lymphoma 2 (referred to herein as "BCL-2") inhibitor.

In an aspect, provided herein is a pharmaceutical combination comprising:

(a) a histone deacetylase 6 (HDAC6) inhibitor of Formula I:

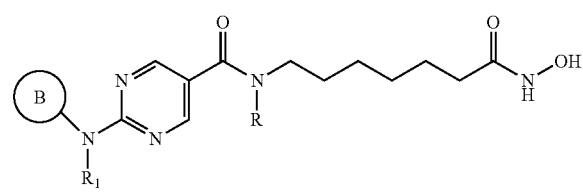

(I)

or a pharmaceutically acceptable salt thereof, wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl; and
(b) a BCL-2 inhibitor.

In various embodiments of the pharmaceutical combination, ring B is aryl.

In various embodiments of the pharmaceutical combination, $R_1$ is aryl or heteroaryl, each of which may be optionally substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by halo.

In yet another embodiment of Formula I, $R_1$ is phenyl that is substituted by chloro.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In various embodiments of the pharmaceutical combination, the HDAC6 inhibitor of Formula I is:

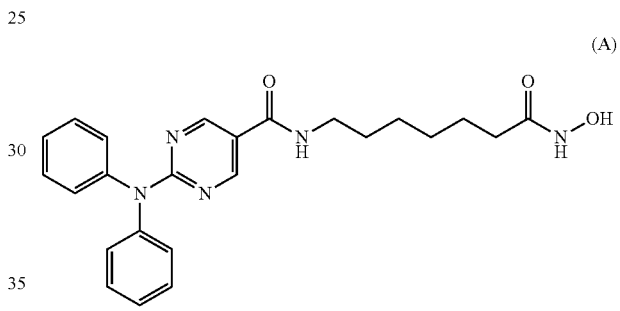

(A)

or a pharmaceutical acceptable salt thereof.

In various embodiments of the pharmaceutical combination, the HDAC6 inhibitor of Formula I is:

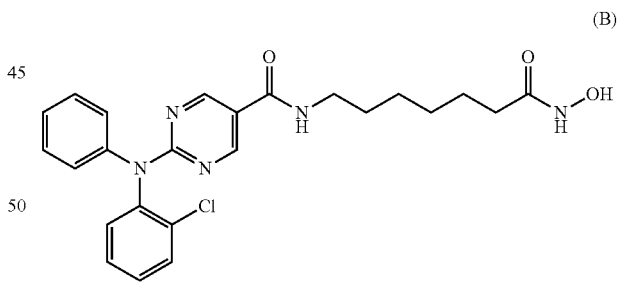

(B)

or a pharmaceutically acceptable salt thereof.

In various embodiments of the pharmaceutical combination, the BCL-2 inhibitor is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl] sulfonyl]benzamide (navitoclax or ABT-263); tetrocarcin A; antimycin; gossypol (e.g., (–)-gossypol acetic acid); obatoclax; ethyl 2-amino-6-bromo-4-(1-cyano-2-ethoxy-2-oxoethyl)-4H-chromene-3-carboxylate (HA 14-1); oblimersen; a Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl]propyl]

amino]-3-nitrophenyl]sulfonyl]-benzamide (ABT-737); 2-((1H-pyrrolo[2,3-b]pyridin-5-yl)oxy)-4-(4-4((4'-chloro-5,5-dimethyl-3,4,5,6-tetrahydro-[1,1'-biphenyl]-2-yl)methyl)piperazin-1-yl)-N-((3-nitro-4-((((tetrahydro-2H-pyran-4-yl)methyl)amino)phenyl)sulfonyl)benzamide (venetoclax); and S55746 (BCL201), or pharamceutically acceptable salts thereof.

In various embodiments of the pharmaceutical combination, the BCL-2 inhibitor is venetoclax, or a pharmaceutically acceptable salt thereof.

In various embodiments of the pharmaceutical combination, the HDAC6 inhibitor and the BCL-2 inhibitor are in the same formulation. In other embodiments of the pharmaceutical combination, the HDAC6 inhibitor and the BCL-2 inhibitor are in separate formulations.

In various embodiments of the pharmaceutical combination, the combination is for simultaneous or sequential administration.

In various embodiments, the pharmaceutical combination is for use in treating cancer in a subject in need thereof.

In other various embodiments, the pharmaceutical combinantion is for use in the preparation of a medicament for the treatment of cancer.

In various embdoiments of the pharmaceutical combination, the cancer is a hematologic cancer.

In various embodiments of the pharmaceutical combination, the cancer is acute myelogenous leukemia (AML), chronic lymphocytic leukemia (CLL), non-Hodgkin's lymphoma (e.g., mantle-cell lymphoma), multiple myeloma, or myelodysplastic syndrome (MDS).

In various embodiments of the pharmaceutical combination, the cancer is refractory or resistant to treatment with at least one prior therapy.

In an aspect, provided herein is a method for treating or preventing cancer in a subject in need thereof, comprising administering to the subject a therapeutically effective amount of the pharmaceutical combination provided herein.

In various embodiments of the method, the cancer is a hematologic cancer.

In various embodiments of the method, the cancer is acute myelogenous leukemia (AML), chronic lymphocytic leukemia (CLL), non-Hodgkin's lymphoma (e.g., mantle-cell lymphoma), multiple myeloma, or myelodysplastic syndrome (MDS).

In various embodiments of the method, the cancer is refractory or resistant to treatment with at least one prior therapy.

In various embodiments of the method, the HDAC6 inhibitor and the BCL-2 inhibitor are administered at approximately the same time. In other embodiments of the method, the HDAC6 inhibitor and the BCL-2 inhibitor are administered at different times.

In an aspect, provided herein is a method of decreasing leukemia cell growth and viability, comprising contacting the cell with a pharmaceutical combination provided herein.

In an aspect, provided herein is a pharmaceutical composition comprising
(a) a histone deacetylase 6 (HDAC6) inhibitor of Formula I:

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) a BCL-2 inhibitor.

In an embodiment of the composition, the pharmaceutical composition further comprises one or more excipients.

In an embodiment of the composition, ring B is aryl. In various embodiments, $R_1$ is aryl or heteroaryl, each of which may be optionally substituted by halo.

In another embodiment of the composition, the compound of Formula I is:

(A)

or a pharmaceutical acceptable salt thereof.

In another embodiment of the composition, the compound of Formula I is:

(B)

or a pharmaceutically acceptable salt thereof.

In various embodiments of the composition, the BCL-2 inhibitor is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl] sulfonyl]benzamide (navitoclax or ABT-263); tetrocarcin A; antimycin; gossypol (e.g., (−)-gossypol acetic acid); obatoclax; ethyl 2-amino-6-bromo-4-(1-cyano-2-ethoxy-2-oxoethyl)-4H-chromene-3-carboxylate (HA 14-1); oblimersen; a Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737); 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide (venetoclax); and S55746 (BCL201), or pharamceutically acceptable salts thereof.

In various embodiments of the composition, the BCL-2 inhibitor is venetoclax, or a pharmaceutically acceptable salt thereof.

DETAILED DESCRIPTION

Figure 1A:
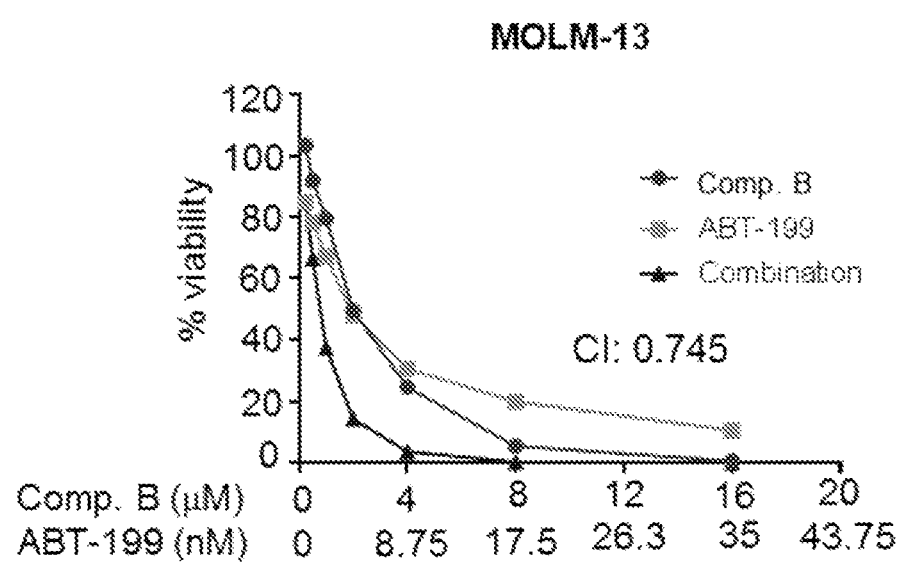
FIGS. 1A, 1B, and 1C show the percent viability of the following cell lines: MOLM-13 (FIG. 1A), Kasumi-1 (FIG. 1B), and MV-4-11 (FIG. 1C), upon exposure to Compound B alone, ABT-199 (also referred to herein as "venetoclax") alone, or the combination of Compound B and ABT-199 at the indicated concentrations.

Provided herein is a pharmaceutical combination comprising a histone deacetylase inhibitor (HDAC) inhibitor and a BCL-2 inhibitor. Specifically, provided herein is a pharmaceutical combination comprising:

(a) a histone deacetylase 6 (HDAC6) inhibitor of Formula I:

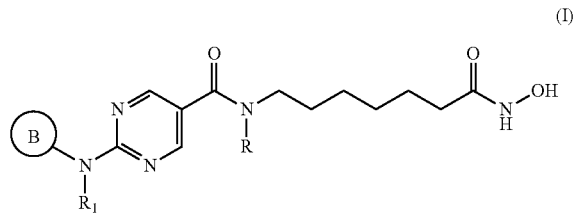

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) a BCL-2 inhibitor, or a pharmaceutically acceptable salt thereof.

Certain terms used herein are described below. Compounds of the present invention are described using standard nomenclature. Unless defined otherwise, all technical and scientific terms used herein have the same meaning as is commonly understood by one of skill in the art to which this invention belongs.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties. The number of carbon atoms in an alkyl substituent can be indicated by the prefix "$C_{x-y}$," where x is the minimum and y is the maximum number of carbon atoms in the substituent.

As used herein, the term "halo" or "halogen" alone or as part of another substituent means, unless otherwise stated, a fluorine, chlorine, bromine, or iodine atom, preferably, fluorine, chlorine, or bromine, more preferably, chlorine.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms. In an embodiment, $C_6$-$C_7$ aryl groups are provided herein.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like. In an embodiment, $C_4$-$C_7$ heteroaryl groups are provided herein.

The term "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety. Unless otherwise specified, or clearly indicated by the text, reference to therapeutic agents useful in the pharmaceutical combination provided herein includes both the free base of the compounds, and all pharmaceutically acceptable salts of the compounds.

The term "pharmaceutically acceptable" as used herein refers to those compounds, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination," "fixed dose," and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that the active ingredients, i.e., the HDAC6 inhibitor and the BCL-2 inhibitor, are administered to a patient as separate entities either simultaneously, concurrently or sequentially with no specific time limits, wherein such administration provides therapeutically effective levels of the two compounds in the body of the subject in need thereof. The latter also applies to cocktail therapy, e.g., the administration of three or more active ingredients.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer.

The term "prevent," "preventing," or "prevention" as used herein comprises the prevention of at least one symptom associated with or caused by the state, disease or disorder being prevented.

The term "pharmaceutically effective amount," "therapeutically effective amount," or "clinically effective amount" of a combination of therapeutic agents is an amount sufficient to provide an observable or clinically significant improvement over the baseline clinically observable signs and symptoms of the disorders treated with the combination.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

As used herein, the term "resistant" or "refractive" to a therapeutic agent when referring to a cancer patient means that the cancer has innate, or achieved, resistance to the effects of the therapeutic agent as a result of contact with the therapeutic agent. Stated alternatively, the cancer is resistant to the ordinary standard of care associated with the particular therapeutic agent.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The terms "about" or "approximately" are generally understood by persons knowledgeable in the relevant subject area, but in certain circumstances can mean within 20%, within 10%, or within 5% of a given value or range. Alternatively, especially in biological systems, the term "about" means within about a log (i.e., an order of magnitude) or within a factor of two of a given value.

The term "synergistic effect" as used herein, refers to action of two agents such as, for example, a compound of Formula I or a pharmaceutically acceptable salt thereof, and a BCL-2 inhibitor (e.g., venetoclax), to produce an effect, for example, slowing the symptomatic progression of cancer or symptoms thereof, which is greater than the simple addition of the effects of each drug administered by itself. A synergistic effect can be calculated, for example, using suitable methods such as the Sigmoid-Emax equation (Holford, N.

H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. The pharmaceutical combinations provided herein, exhibit synergistic effects in connection with cell growth and viability in connection with leukemia cell lines (see, e.g., Examples 3 and 4). In some embodiments, the pharmaceutical combinations provided herein are given in amounts that result in synergistic effects. In some embodiments, the pharmaceutical combinations provided herein are given in amounts that result in greater than additive effects.

The term "histone deacetylase" or "HDAC" refers to enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "histone deacetylase inhibitor" (HDAC inhibitors, HDACi, HDIs) as used herein refers to a compound that selectively targets, decreases, or inhibits at least one activity of a histone deacetylase.

Histone Deacetylase Inhibitors

Provided herein are pharmaceutical combinations comprising a histone deacetylase 6 (HDAC6) inhibitor of Formula I (also referred to herein as "compounds of Formula I"):

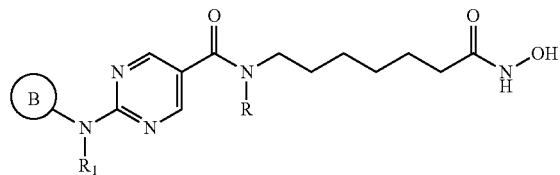

(I)

or a pharmaceutically acceptable salt thereof, wherein,
ring B is aryl or heteroaryl;
$R_1$ is aryl or heteroaryl, each of which may be optionally substituted by OH, halo, or $C_{1-6}$-alkyl; and
R is H or $C_{1-6}$-alkyl.

In an embodiment of the compound of Formula I, ring B is aryl. In various embodiments, $R_1$ is aryl or heteroaryl, each of which may be optionally substituted by halo.

In an embodiment of Formula I, $R_1$ is an aryl that is substituted by OH, halo, or $C_{1-6}$-alkyl.

In another embodiment of Formula I, $R_1$ is $C_5$-$C_7$ aryl that is substituted by OH, halo, or $C_{1-6}$-alkyl.

In another embodiment of Formula I, $R_1$ is $C_4$-$C_7$ heteroaryl that is substituted by OH, halo, or $C_{1-6}$-alkyl.

In yet another embodiment of Formula I, $R_1$ is phenyl that is substituted by OH, halo, or $C_{1-6}$-alkyl.

In yet another embodiment of Formula I, $R_1$ is phenyl that is substituted by halo.

In yet another embodiment of Formula I, $R_1$ is phenyl that is substituted by chloro.

In another embodiment of Formula I, ring B is $C_5$-$C_7$ aryl.

In another embodiment of Formula I, ring B is $C_4$-$C_7$ heteroaryl.

In yet another embodiment of Formula I, ring B is phenyl.

In a specific embodiment, the compound of Formula I is Compound A, or a pharmaceutically acceptable salt thereof, or Compound B, or a pharmaceutically acceptable salt thereof, as shown in Table 1:

TABLE 1

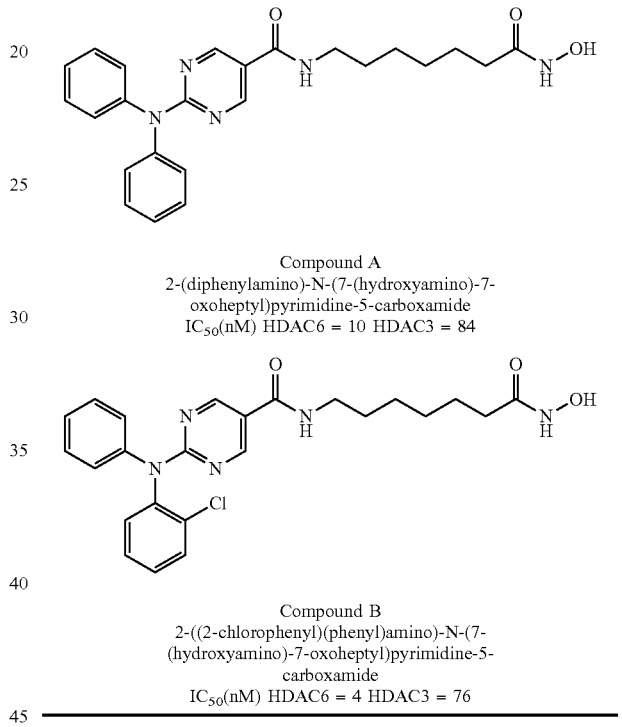

Compound A
2-(diphenylamino)-N-(7-(hydroxyamino)-7-oxoheptyl)pyrimidine-5-carboxamide
$IC_{50}$(nM) HDAC6 = 10 HDAC3 = 84

Compound B
2-((2-chlorophenyl)(phenyl)amino)-N-(7-(hydroxyamino)-7-oxoheptyl)pyrimidine-5-carboxamide
$IC_{50}$(nM) HDAC6 = 4 HDAC3 = 76

For convenience, the group of the histone deacetylase 6 inhibitors of Formula I and its salts are collectively referred to to as compounds of Formula I, meaning that reference to compounds of Formula I will refer to any of the compounds or pharmaceutically acceptable salt thereof in the alternative.

Compounds of Formula I (e.g., Compounds A and B) are known HDAC6 inhibitors, and are described in PCT Pub. No. WO2011/091213, the content of which is incorporated herein by reference in its entirety. Compounds A and B are currently being investigated in Phase 1b clinical development for the treatment of multiple myeloma.

The preparation of Compounds A and B are also described herein as Example 1. Preferably, Compounds A and B are in the free base form.

The salts of compounds of Formula I are preferably pharmaceutically acceptable salts; suitable counter-ions forming pharmaceutically acceptable salts are known in the field.

BCL-2 Inhibitors

The term "BCL-2 inhibitor" as used herein, refers to a compound that selectively targets, decreases, or inhibits at least one activity of BCL-2. The B-cell lymphoma 2 (Bcl-2)

family of proteins are key regulators of the mitochondrial (also called "intrinsic") pathway of apoptosis. See, Danial, N. N. and Korsmeyer, S. J. Cell (2004) 116, 205-219. Misregulation of BCL-2 is implicated in a wide variety of cancers, particularly hematological cancers such as follicular lymphoma, diffuse large cell lymphoma, and chronic lymphocytic leukemia. Adams, J. M. and Cory, S. Science (1998) 281, 1322-1326.

Non-limiting examples of BCL-2 inhibitors include, e.g., 4-[4-[[2-(4-chlorophenyl)-5,5-di methyl-1-cyclohexen-1-yl] methyl]-1-piperazinyl]-N-[[4-[[(1R)-3-(4-morpholinyl)-1-[(phenylthio)methyl]propyl]amino]-3-[(trifluoromethyl) sulfonyl]phenyl] sulfonyl]benzamide (navitoclax or ABT-263); tetrocarcin A; antimycin; gossypol (e.g., (−)-gossypol acetic acid); obatoclax (GX15-070); ethyl 2-amino-6-bromo-4-(1-cyano-2-ethoxy-2-oxoethyl)-4H-chromene-3-carboxylate (HA 14-1); oblimersen; a Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl] propyl]amino]-3-nitrophenyl]sulfonyl]-benzamide (ABT-737); 2-((1H-pyrrolo[2,3-b]pyridin-5-yl)oxy)-4-(44(4'-chloro-5,5-dimethyl-3,4,5,6-tetrahydro-[1,1'-biphenyl]-2-Amethyl)piperazin-l-yl)-N-((3-nitro-4-(((tetrahydro-2H-pyran-4-Amethyl)amino)phenyl)sulfonyl)benzamide (venetoclax); and S55746 (BCL201).

Any of these BCL-2 inhibitors can be used in the pharmaceutical combinations provided herein.

Structures of certain BCL-2 inhibitors are shown in Table 2:

TABLE 2

| BCL-2 inhibitor | Structure |
|---|---|
| navitoclax | 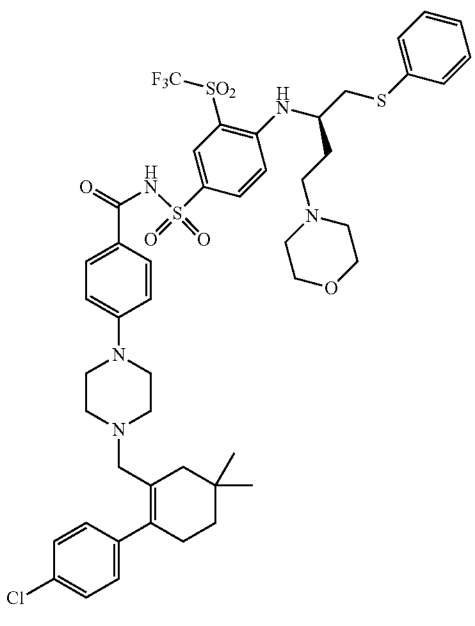 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1] |
| obatoclax | 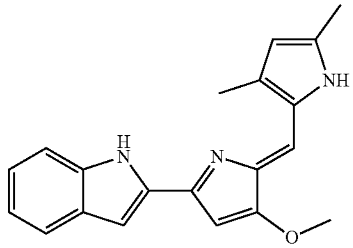 [SMILES: COC1=CC(c2cc3ccccc3[nH]2)=N/C1=C\c1[nH]c(C)cc1C] |

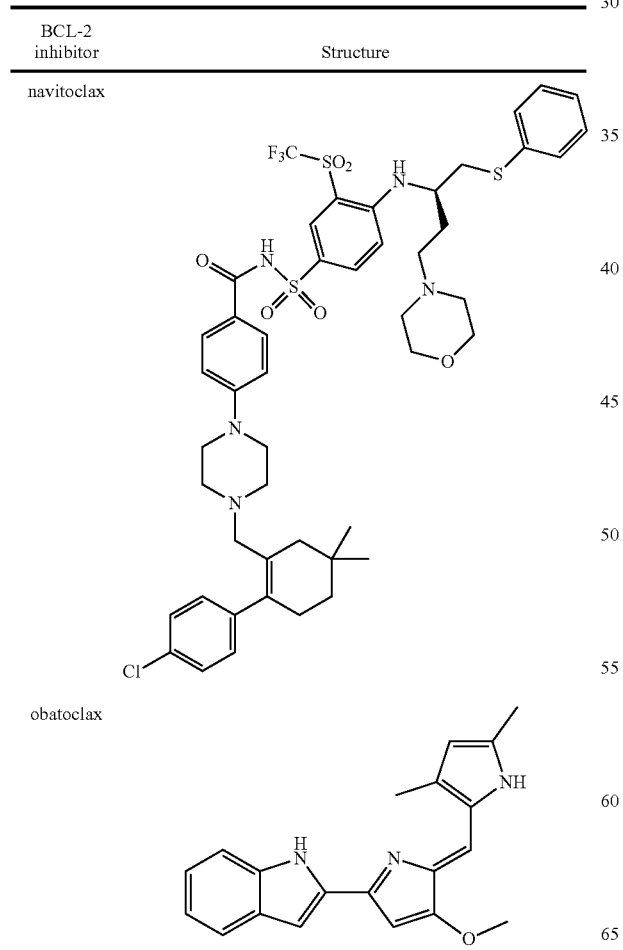

TABLE 2-continued

| BCL-2 inhibitor | Structure |
|---|---|
| HA 14-1 | 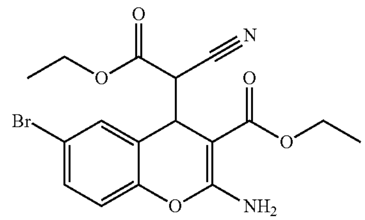 [SMILES: CCOC(=O)C1=C(N)Oc2ccc(Br)cc2C1C(C#N)C(=O)OCC] |
| ABT-737 | 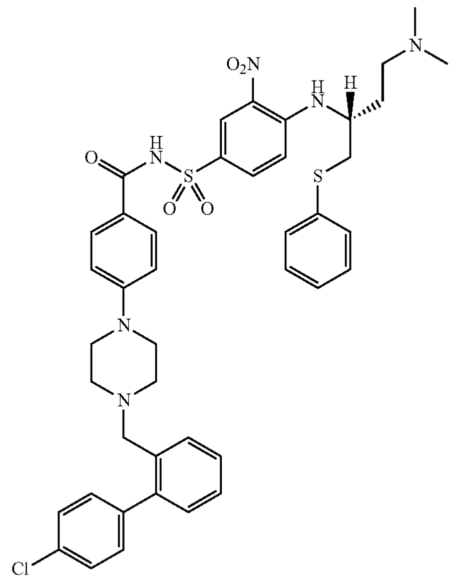 [SMILES: CN(C)CC[C@H](CSc1ccccc1)Nc1ccc(S(=O)(=O)NC(=O)c2ccc(N3CCN(Cc4ccccc4-c4ccc(Cl)cc4)CC3)cc2)cc1[N+](=O)[O-]] |
| venetoclax | 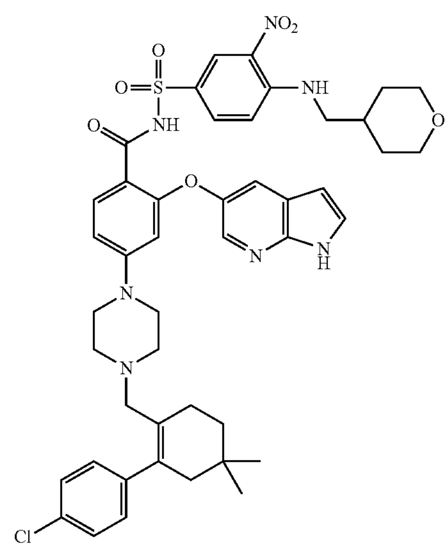 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |

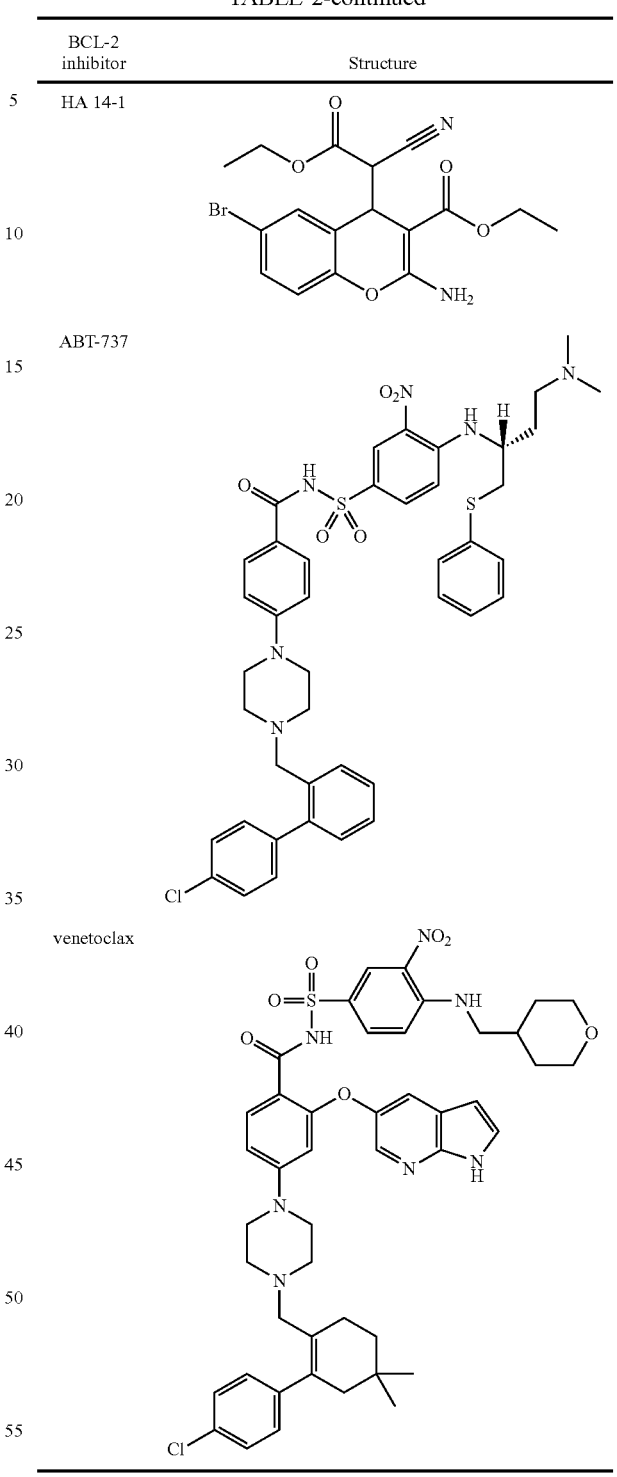

In an embodiment, the BCL-2 inhibitor is a compound shown in Table 2, or a pharmaceutically acceptable salt thereof.

In a particular embodiment, the BCL-2 inhibitor is venetoclax (also referred to as "ABT-199"), or a pharmaceutically acceptable salt thereof.

Venetoclax is approved by the FDA for the treatment of patients with chronic lymphocytic leukemia (CLL) with 17p deletion, as detected by an FDA approved test, who have received at least one prior therapy (see, e.g., the FDA label for VENCLEXTA™ http://www.accessdata.fda.gov/drugs-atfda_docs/label/2016/208573s000lbl.pdf).

In another particular embodiment, the BCL-2 inhibitor is S55746. S55746 is currently being studied in clinical trials for patients with chronic lymphocytic leukemia (CLL), B-cell non-Hodgkin's lymphoma, or multiple myeloma. (see, e.g., https://clinicaltrials.gov/ct2/show/NCT029-20697). In another embodiment, the BCL-2 inhibitor is navitoclax. In another embodiment, the BCL-2 inhibitor is ABT-737, or a pharmaceutically acceptable salt thereof. In another embodiment, the BCL-2 inhibitor is HA-14-1, or a pharmaceutically acceptable salt thereof. In another embodiment, the BCL-2 inhibitor is obatoclax, or a pharmaceutically acceptable salt thereof. In another embodiment, the BCL-2 inhibitor is oblemerson, or a pharmaceutically acceptable salt thereof. In another embodiment, the BCL-2 inhibitor is tetrocarcin A, or a pharmaceutically acceptable salt thereof. In another embodiment, the BCL-2 inhibitor is BAK BH3 peptide, or a pharmaceutically acceptable salt thereof. In another embodiment, the BCL-2 inhibitor is antimycin, or a pharmaceutically acceptable salt thereof. In another embodiment, the BCL-2 inhibitor is antimycin, or a pharmaceutically acceptable salt thereof. In another embodiment, the BCL-2 inhibitor is gossypol, or a pharmaceutically acceptable salt thereof.

Data provided herein shows that the combination therapy provided herein (e.g., HDAC6 inhibitors and a BCL-2 inhibitor) synergistically reduced the viability of certain cancer cell lines (see, e.g., Example 3). Further, the combination therapy provided herein synergistically increases apoptosis of certain cancer cell lines (see, e.g., Example 4).

Compounds of Formula I or the BCL-2 inhibitor, or both, can be administered in free form or in pharmaceutically acceptable salt form.

Also provided herein is a commercial package comprising, as therapeutic agents, the combination provided herein, together with instructions for simultaneous, separate or sequential administration thereof for use in the delay of progression or treatment of a cancer.

Methods for Treating

Provided herein is a method for treating or preventing cancer in a subject in need thereof comprising administering to the subject a therapeutically effective amount of a pharmaceutical combination provided herein, i.e., a pharmaceutical combination comprising:

(a) a histone deacetylase 6 (HDAC6) inhibitor of Formula I:

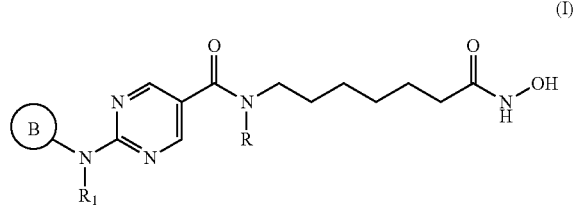

or a pharmaceutically acceptable salt thereof,
wherein,
ring B is aryl or heteroaryl;
$R_1$ is aryl or heteroaryl, each of which may be optionally substituted by OH, halo, or $C_{1-6}$ alkyl;
and
R is H or $C_{1-6}$-alkyl; and
(b) a BCL-2 inhibitor, or a pharmaceutically acceptable salt thereof.

In an embodiment, provided herein is a method for treating cancer in a subject in need thereof comprising administering to the subject a therapeutically effective amount of a pharmaceutical combination provided herein.

In a specific embodiment of the methods, the HDAC6 inhibitor is Compound B, or a pharmaceutically acceptable salt thereof; and the BCL-2 inhibitor is venetoclax, or a pharmaceutically acceptable salt thereof.

The methods provided herein can be used for both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In various embodiments of the method, the cancer is a hematologic cancer. Hematologic cancers include leukemias, lymphomas, and myelomas.

In various embodiments of the method, the cancer is acute myelogenous leukemia (AML), chronic lymphocytic leukemia (CLL), non-Hodgkin's lymphoma, multiple myeloma, or myelodysplastic syndrome (MDS). In a further embodiment, the cancer is mantle-cell lymphoma (MCL). In yet a further embodiment, the cancer is a B-cell lymphoma. In various embodiments of the method, the cancer is refractory or resistant to treatment with at least one prior therapy.

In one embodiment, provided herein is a method for treating a cancer in a subject in need thereof, comprising administering to the subject a therapeutically effective amount of an HDAC inhibitor of Formula I, or a pharmaceutically acceptable salt thereof, and a therapeutically effective amount of a BCL-2 inhibitor. In some embodiments, provided herein is a method for treating a cancer in a subject in need thereof, comprising administering to the subject a therapeutically effective amount of Compound A, or a pharmaceutically acceptable salt thereof, and a therapeutically effective amount of a BCL-2 inhibitor.

In another embodiment, provided herein is a method for treating a hematological cancer in a subject in need thereof, comprising administering to the subject a therapeutically effective amount of an HDAC inhibitor of Formula I, or a pharmaceutically acceptable salt thereof, and a therapeutically effective amount of a BCL-2 inhibitor, or a pharmaceutically acceptable salt thereof. In some embodiments, provided herein is a method for treating a hematological cancer in a subject in need thereof, comprising administering to the subject a therapeutically effective amount of Compound A, or a pharmaceutically acceptable salt thereof, and a therapeutically effective amount of a BCL-2 inhibitor, or a pharmaceutically acceptable salt thereof.

In another embodiment, provided herein is a method for treating a leukemia in a subject in need thereof, comprising administering to the subject a therapeutically effective amount of an HDAC inhibitor of Formula I, or a pharmaceutically acceptable salt thereof, and a therapeutically effective amount of a BCL-2 inhibitor, or a pharmaceutically acceptable salt thereof. In some embodiments, provided herein is a method for treating a leukemia in a subject in need thereof, comprising administering to the subject a therapeutically effective amount of Compound A, or a pharmaceutically acceptable salt thereof, and a therapeutically effective amount of a BCL-2 inhibitor, or a pharmaceutically acceptable salt thereof.

In another embodiment is a method for treating a cancer in a subject in need thereof, comprising administering to the subject a therapeutically effective amount of Compound A, or a pharmaceutically acceptable salt thereof, and a therapeutically effective amount of venetoclax, or a pharmaceutically acceptable salt thereof. This embodiment exhibits synergy such that sub-therapeutic amounts of Compound A or of venetoclax can be used in the method.

In another embodiment is a method for treating a hematological cancer in a subject in need thereof, comprising administering to the subject a therapeutically effective amount of Compound A, or a pharmaceutically acceptable salt thereof, and a therapeutically effective amount of venetoclax, or a pharmaceutically acceptable salt thereof. In another embodiment is a method for treating a leukemia in a subject in need thereof, comprising administering to the subject a therapeutically effective amount of Compound A, or a pharmaceutically acceptable salt thereof, and a therapeutically effective amount of venetoclax, or a pharmaceutically acceptable salt thereof.

In yet another embodiment is a method for treating a cancer in a subject in need thereof, comprising administering to the subject a therapeutically effective amount of Compound A, or a pharmaceutically acceptable salt thereof, and a therapeutically effective amount of a BCL-2 inhibitor selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl] sulfonyl]benzamide (navitoclax or ABT-263); tetrocarcin A; antimycin; gossypol; obatoclax; ethyl 2-amino-6-bromo-4-(1-cyano-2-ethoxy-2-oxoethyl)-4H-chromene-3-carboxylate (HA 14-1); oblimersen; Bak BH3 peptide; 4-[4-[(4'-chloro[1,1'-biphenyl]-2-Amethyl]-1-piperazinyl]-N-[[4-[[(1R)-3-(dimethylamino)-1-[(phenylthio)methyl]propyl]amino]-3-nitrophenyl]sulfonyl]-benzamide (ABT-737); 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide (venetoclax); and S55746 (BCL201), or pharamceutically acceptable salts thereof.

In other embodiments, provided herein is a method for treating a cancer in a subject in need thereof, comprising administering to the subject a therapeutically effective amount of Compound B, or a pharmaceutically acceptable salt thereof, and a therapeutically effective amount of a BCL-2 inhibitor, or a pharmaceutically acceptable salt thereof. In some embodiments, the method comprises administering to the subject a therapeutically effective amount of Compound B, or a pharmaceutically acceptable salt thereof, and a therapeutically effective amount of a BCL-2 inhibitor selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl] sulfonyl]benzamide (navitoclax or ABT-263); tetrocarcin A; antimycin; gossypol; obatoclax; ethyl 2-amino-6-bromo-4-(1-cyano-2-ethoxy-2-oxoethyl)-4H-chromene-3-carboxylate (HA 14-1); oblimersen; Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737); 2-((1H-pyrrolo[2,3-b]pyridin-5-yl)oxy)-4-((4'-chloro-5,5-dimethyl-3,4,5,6-tetrahydro-[1,1'-biphenyl]-2-Amethyl)piperazin-1-yl)-N-((3-nitro-4-(((tetrahydro-2H-pyran-4-Amethyl)amino)phenyl)sulfonyl)benzamide (venetoclax); and S55746 (BCL201), or pharamceutically acceptable salts thereof.

In some embodiments, provided herein is a method for treating a hematological cancer in a subject in need thereof, comprising administering to the subject a therapeutically effective amount of Compound B, or a pharmaceutically acceptable salt thereof, and a therapeutically effective amount of a BCL-2 inhibitor, or a pharmaceutically acceptable salt thereof. In some embodiments, provided herein is a method for treating a leukemia in a subject in need thereof, comprising administering to the subject a therapeutically effective amount of Compound B, or a pharmaceutically acceptable salt thereof, and a therapeutically effective amount of a BCL-2 inhibitor, or a pharmaceutically acceptable salt thereof.

In another embodiment is a method for treating a cancer in a subject in need thereof, comprising administering to the subject a therapeutically effective amount of Compound B, or a pharmaceutically acceptable salt thereof, and a therapeutically effective amount of venetoclax, or a pharmaceutically acceptable salt thereof. This embodiment exhibits synergy such that sub-therapeutic amounts of Compound B or of venetoclax can be used in the method.

In another embodiment is a method for treating a hematological cancer in a subject in need thereof, comprising administering to the subject a therapeutically effective amount of Compound B, or a pharmaceutically acceptable salt thereof, and a therapeutically effective amount of venetoclax, or a pharmaceutically acceptable salt thereof.

In another embodiment is a method for treating a leukemia in a subject in need thereof, comprising administering to the subject a therapeutically effective amount of Compound B, or a pharmaceutically acceptable salt thereof, and a therapeutically effective amount of venetoclax, or a pharmaceutically acceptable salt thereof.

The subject considered herein is typically a human. However, the subject can be any mammal for which treatment is desired. Thus, the methods described herein can be applied to both human and veterinary applications.

Pharmaceutical Combinations and Compositions

Provided herein is a pharmaceutical combination comprising a histone deacetylase inhibitor (HDAC) inhibitor and a BCL-2 inhibitor.

In an aspect, provided herein is a pharmaceutical combination comprising:

(a) a histone deacetylase 6 (HDAC6) inhibitor of Formula I:

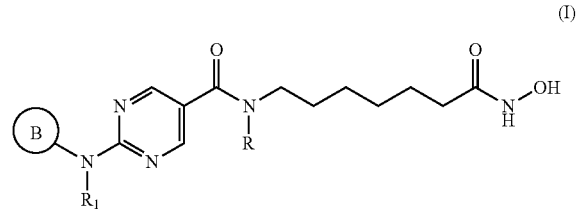

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) a BCL-2 inhibitor, or a pharmaceutically acceptable salt thereof.

In various embodiments of the pharmaceutical combination, ring B is aryl.

In various embodiments of the pharmaceutical combination, $R_1$ is aryl or heteroaryl, each of which may be optionally substituted by halo.

In various embodiments of the pharmaceutical combination, the compound of Formula I is Compound A, or a pharmaceutically acceptable salt thereof. In another embodiment, the compound of Formula I is Compound B, or a pharmaceutically acceptable salt thereof.

In various embodiments of the pharmaceutical combination, the BCL-2 inhibitor is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[((trifluoromethyl)sulfonyl]phenyl] sulfonyl]benzamide (navitoclax or ABT-263); tetrocarcin A; antimycin; gossypol (e.g., (−)-gossypol acetic acid); obatoclax; ethyl 2-amino-6-bromo-4-(1-cyano-2-ethoxy-2-oxoethyl)-4H-chromene-3-carboxylate (HA 14-1); oblimersen; a Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737); 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl) piperazin-1-yl)-N-((3-nitro-4-(((tetrahydro-2H-pyran-4-yl) methyl)amino)phenyl)sulfonyl)benzamide (venetoclax); and S55746 (BCL201), or pharamceutically acceptable salts thereof.

In various embodiments of the pharmaceutical combination, the BCL-2 inhibitor is venetoclax, or a pharmaceutically acceptable salt thereof.

In a specific embodiment of the pharmaceutical combination, the HDAC6 inhibitor is Compound B, or a pharmaceutically acceptable salt thereof and the BCL-2 inhibitor is venetoclax.

In various embodiments of the pharmaceutical combination, the HDAC6 inhibitor and the BCL-2 inhibitor are in the same formulation. In other embodiments of the pharmaceutical combination, the HDAC6 inhibitor and the BCL-2 inhibitor are in separate formulations.

In various embodiments of the pharmaceutical combination, the combination is for simultaneous or sequential administration.

In various embodiments, the pharmaceutical combination is for use in treating cancer in a subject in need thereof.

In an embodiment, the combination of the invention is used for the treatment or prevention of cancer comprising administering to the subject a combination therapy, comprising an effective amount of the HDAC6 inhibitor (i.e., compounds of Formula I) and an effective amount of the BCL-2 inhibitor. Preferably, these compounds are administered at therapeutically effective dosages which, when combined, provide a beneficial effect. The administration can comprise the separate administration of each component, either simultaneously, or sequentially.

In various embodiments, the pharmaceutical combination is for use in the preparation of a medicament for the treatment or prevention of cancer. In a further embodiment, the pharmaceutical combination is for use in the preparation of a medicament for the treatment of cancer.

The pharmaceutical combination provided herein can also inhibit the growth of both solid tumors and liquid tumors. Further, depending on the tumor type and particular combination used, a decrease of the tumor volume can be obtained. The combination disclosed herein is also suited to prevent the metastatic spread of tumors and the growth or development of micrometastases. The combination disclosed herein is suitable for the treatment of poor prognosis patients.

In other various embodiments, the pharmaceutical combination is for use in the preparation of a medicament for the treatment of cancer.

In various embodiments of the pharmaceutical combination, the cancer is a hematologic cancer. Hematologic cancers include leukemias, lymphomas, and myelomas.

In various embodiments of the pharmaceutical combination, the cancer is acute myelogenous leukemia (AML), chronic lymphocytic leukemia (CLL), non-Hodgkin's lymphoma, multiple myeloma, or myelodysplastic syndrome (MDS). In a further embodiment, the cancer is mantle-cell lymphoma (MCL). In yet a further embodiment, the cancer is a B-cell lymphoma.

In various embodiments of the pharmaceutical combination, the cancer is refractory or resistant to treatment with at least one prior therapy.

Provided herein are pharmaceutical compositions comprising a histone deacetylase inhibitor (HDAC) inhibitor and a BCL-2 inhibitor.

As used herein, the term "pharmaceutical composition" is defined herein to refer to a mixture or solution containing the therapeutic agent(s) to be administered to a subject, e.g., a mammal or human, in order to prevent or treat a particular disease or condition affecting the mammal.

In an aspect, provided herein is a pharmaceutical composition comprising:

(a) a histone deacetylase 6 (HDAC6) inhibitor of Formula I:

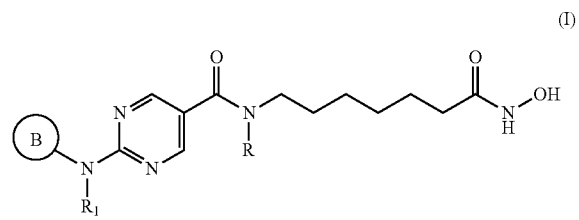

(I)

or a pharmaceutically acceptable salt thereof,
wherein,
ring B is aryl or heteroaryl;
$R_1$ is aryl or heteroaryl, each of which may be optionally substituted by OH, halo, or $C_{1-6}$-alkyl;
and
R is H or $C_{1-6}$-alkyl; and
(b) a BCL-2 inhibitor.

In an embodiment of the composition, ring B is aryl. In various embodiments, $R_1$ is aryl or heteroaryl, each of which may be optionally substituted by halo.

In another embodiment of the composition, the compound of Formula I is Compound A, or a pharmaceutically acceptable salt thereof. In another embodiment of the composition, the compound of Formula I is Compound B, or a pharmaceutically acceptable salt thereof.

In various embodiments of the composition, the BCL-2 inhibitor is selected from the group consisting of 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl] phenyl] sulfonyl]benzamide (navitoclax or ABT-263); tetrocarcin A; antimycin; gossypol (e.g., (−)-gossypol acetic acid); obatoclax; ethyl 2-amino-6-bromo-4-(1-cyano-2- ethoxy-2-oxoethyl)-4H-chromene-3-carboxylate (HA 14-1); oblimersen; a Bak BH3 peptide; 4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide (ABT-737); 2-((1H-pyrrolo[2,3-b] pyridin-5-yl)oxy)-4-(4-((4'-chloro-5,5-dimethyl-3,4,5,6-tetrahydro-[1,1'-biphenyl]-2-(yl)methyl)piperazin-1-yl)-N-((3-nitro-4-(((tetrahydro-2H-pyran-4-yl)ethyl)amino) phenyl)sulfonyl)benzamide (venetoclax); and S55746 (BCL201), or pharamceutically acceptable salts thereof.

In various embodiments of the composition, the BCL-2 inhibitor is venetoclax, or a pharmaceutically acceptable salt thereof.

In a specific embodiment of the composition, the compound of Formula I is Compound A, or a pharmaceutically acceptable salt thereof, and the BCL-2 inhibitor is venetoclax, or a pharmaceutically acceptable salt thereof.

In a specific embodiment of the composition, the compound of Formula I is Compound B, or a pharmaceutically acceptable salt thereof, and the BCL-2 inhibitor is venetoclax, or a pharmaceutically acceptable salt thereof.

In an embodiment of the composition, the pharmaceutical composition further comprises one or more excipients. As used herein, the term "pharmaceutically acceptable excipient" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical composition may contain, from about 0.1% to about 99.9%, preferably from about 1% to about 60%, of the therapeutic agent(s).

Suitable pharmaceutical compositions for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, direct compression, granulating, sugar-coating, dissolving, lyophilizing processes, melt granulation, or fabrication techniques readily apparent to those skilled in the art. It will be appreciated that the unit content of a combination partner contained in an individual dose of each dosage form need not in itself constitute an effective amount since the necessary effective amount may be reached by administration of a plurality of dosage units.

Administration/Dose

The method of treating cancer according to the disclosure provided herein can comprise (i) administration of the HDAC6 inhibitor (a) in free or pharmaceutically acceptable salt form and (ii) administration of the BCL-2 inhibitor (b) in free or pharmaceutically acceptable salt form simultaneously or sequentially, in any order, in jointly therapeutically effective amounts, preferably in synergistically effective amounts, e.g., in daily or intermittent dosages. The individual combination partners of the pharmaceutical combination provided herein can be administered separately at different times during the course of therapy or concurrently in divided or single combination forms. The method provided herein is therefore to be understood as embracing all such regimens of simultaneous or alternating treatment and the term "administering" is to be interpreted accordingly.

For example, in one embodiment of the method, the HDAC6 inhibitor is administered first, followed by the BCL-2 inhibitor. In another embodiment of the method, the BCL-2 inhibitor is administered first, followed by the HDAC6 inhibitor.

Compounds of Formula I can be orally administered in an amount from about 10 mg to about 1000 mg (including e.g., about 10 mg to about 500 mg) per day in single or multiple doses. Thus, in an embodiment of the methods of treatment provided herein, the compound of Formula I is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the compound of Formula I is administered at a dosage of about 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg per day. In an embodiment of the pharmaceutical combination, Compound A is in an amount from 600 mg to 3000 mg (e.g., about 600, about 800, about 1000, about 1200, about 1400, about 1600, about 1800, about 2000 mg). In a further embodiment of the pharmaceutical combination, Compound A is in an amount from 600 mg to 2000 mg. In a preferred embodiment of the pharmaceutical combination, Compound A is in an amount from 180 mg to 480 mg.

In another embodiment of the pharmaceutical combination, Compound A is in an amount from 5 mg to 600 mg (e.g., about 5, about 25, about 50, about 100, about 200, about 300, about 400, about 500, about 600 mg). In yet another embodiment of the pharmaceutical combination Compound A is 10 mg to 200 mg.

In an embodiment of the pharmaceutical combination, Compound B is in an amount from 600 mg to 3000 mg (e.g., about 600, about 800, about 1000, about 1200, about 1400, about 1600, about 1800, about 2000 mg). In a further embodiment of the pharmaceutical combination, Compound B is in an amount from 600 mg to 2000 mg. In a preferred embodiment of the pharmaceutical combination, Compound B is in an amount from 180 mg to 480 mg.

In another embodiment of the pharmaceutical combination, Compound B is in an amount from 5 mg to 600 mg (e.g., about 5, about 25, about 50, about 100, about 200, about 300, about 400, about 500, about 600 mg). In yet another embodiment of the pharmaceutical combination Compound B is 10 mg to 200 mg.

In an embodiment of the combination therapy provided herein, venetoclax is administered orally. In a further embodiment, the daily dosage of venetoclax is between about 10 and about 500 mg per day (including e.g., about 10 mg to about 400 mg, about 10 mg to about 300 mg, or about 10 mg to about 200 mg) per day in single or multiple doses. In other embodiments of the combination therapy provided herein, the BCL-2 inhibitor (e.g., venetoclax) is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the BCL-2 inhibitor is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, or 200 mg per day. In an embodiment of the pharmaceutical combination, the ratio of the compound of Formula I to the BCL-2 inhibitor is in the range of 700:1-1:40. In another embodiment, the ratio of the compound of Formula I to the BCL-2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound A to the BCL-2 inhibitor is in the range of 700:1-1:40. In another embodiment, the ratio of Compound A to the BCL-2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; 4:1 to 1:1, for example, 4:1, 3:1, 2:1 or 1:1; or 30:1 to 10:1, for example, 30:1, 20:1 or 10:1.

In another embodiment of the pharmaceutical combination, the ratio of Compound B to the BCL-2 inhibitor is in the range of 700:1-1:40. In another embodiment, the ratio of Compound B to the BCL-2 inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to venetoclax is in the range of 700:1-1:40. In another embodiment, the ratio of Compound A to venetoclax is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound B to venetoclax is in the range of 700:1-1:40. In another embodiment, the ratio of Compound B to venetoclax is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

It can be shown by established test models that a pharmceutical combination as provided herein results in the beneficial effects described herein before. The person skilled in the art is fully enabled to select a relevant test model to prove such beneficial effects. The pharmacological activity of the pharmaceutical combinations provided herein may, for example, be demonstrated in a clinical study or in an animal model.

In an embodiment, the pharmaceutical combination or composition, or both, provided herein display a synergistic effect.

In a further embodiment, provided herein is a synergistic combination for administration to a subject comprising the combination of the invention, where the dose range of each component corresponds to the synergistic ranges suggested in a suitable tumor model or clinical study.

In determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in certain experiments can be predictive of the effect in other species, and animal models exist that may be used to further quantify a synergistic effect. The results of such studies can also be used to predict effective dose ratio ranges and the absolute doses and plasma concentrations.

In a further embodiment, provided herein is a synergistic combination for administration to a subject comprising the combination of the invention, where the dose range of each component corresponds to the synergistic ranges suggested in a suitable tumor model or clinical study.

The effective dosage of each of the combination partners employed in the combination of the invention may vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient.

The optimum ratios, individual and combined dosages, and concentrations of the combination partners (e.g., compound of Formula I and the BCL-2 inhibitor) of the combination provided herein that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the compounds, but not the other compound of the combination.

When the combination partners, which are employed in the combination of the invention, are applied in the form as marketed as single drugs, their dosage and mode of administration can be in accordance with the information provided on the package insert of the respective marketed drug, if not mentioned herein otherwise.

The optimal dosage of each combination partner for treatment of a cancer can be determined empirically for each individual using known methods and will depend upon a variety of factors, including, though not limited to: the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art. In various embodiments of the pharmaceutical combination, the HDAC6 inhibitor and the BCL-2 inhibitor are in the same formulation. Alternatively, the HDAC6 inhibitor and the BCL-2 inhibitor are in separate formulations.

In various embodiments of the pharmaceutical combination, the combination is for simultaneous or sequential administration.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

EXAMPLES

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1: Synthesis of 2-(diphenylamino)-N-(7-(hydroxyamino)-7-oxoheptyl)pyrimidine-5-carboxamide (Compound A) and 2-((2-chlorophenyl)(phenyl)amino)-N-(7-(hydroxyamino)-7-oxoheptyl)pyrimidine-5-carboxamide (Compound B)

I. Synthesis of 2-(diphenylamino)-N-(7-(hydroxyamino)-7-oxoheptyl)pyrimidine-5-carboxamide (Compound A):

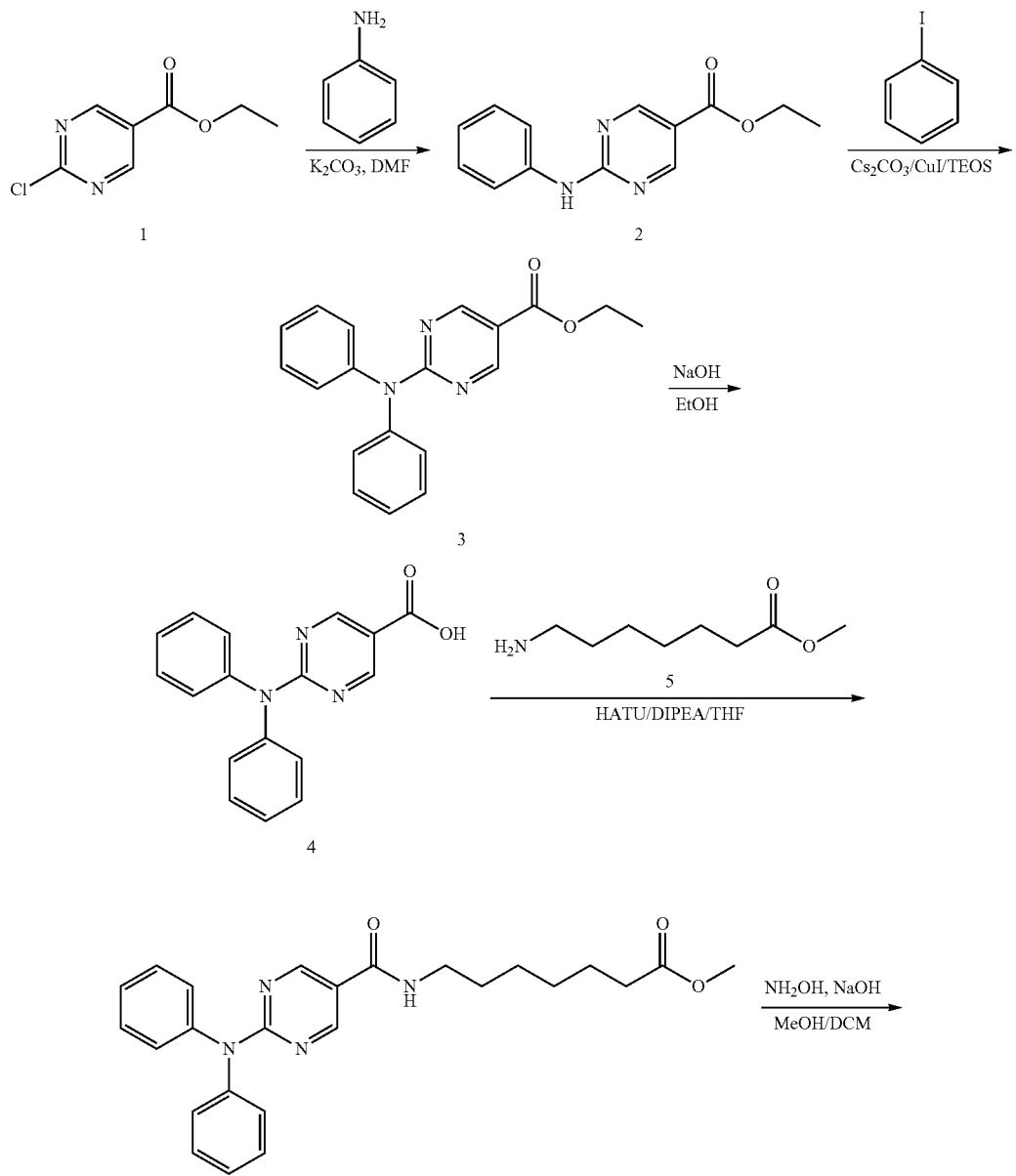

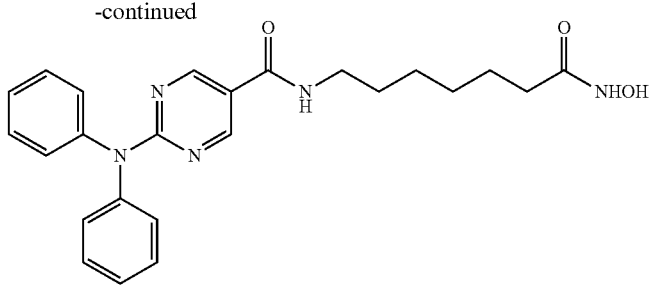

Synthesis of Intermediate 2: A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$-$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over $Na_2SO_4$. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide: A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-H PLC to give a white solid (950 mg, 48%).

II. Synthetic Route 1: 2-((2-chlorophenyl)(phenyl)amino)-N-(7-(hydroxyamino)-7-oxoheptyl)pyrimidine-5-carboxamide (Compound B)

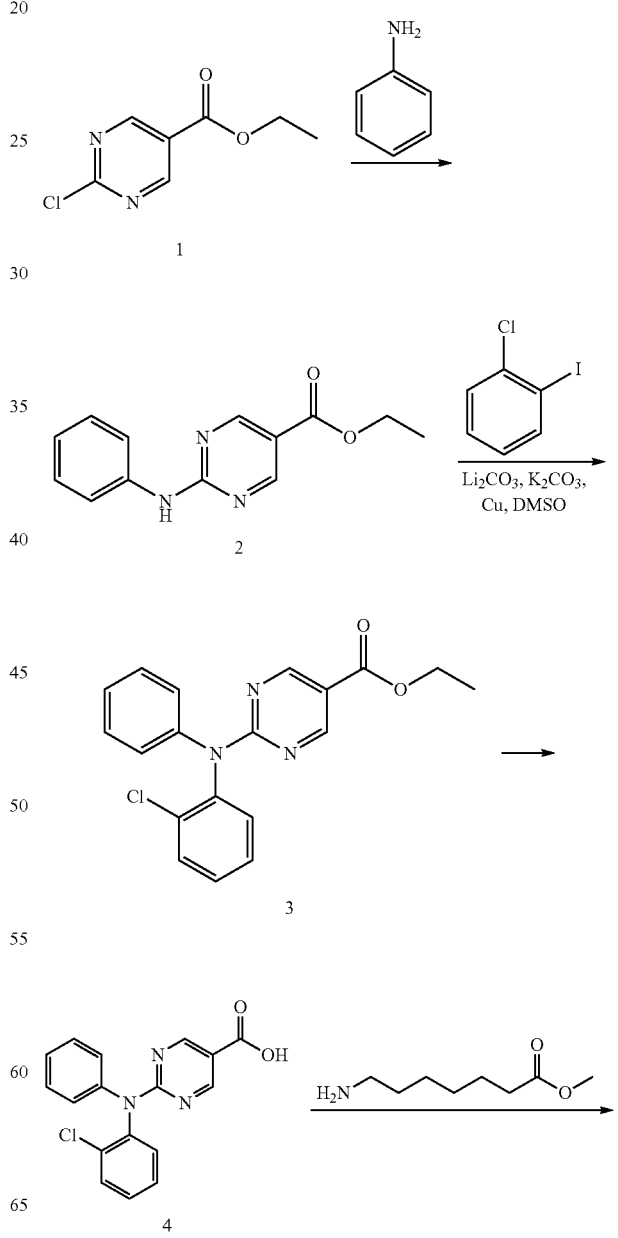

28

III. Synthetic Route 2: 2-((2-chlorophenyl)(phenyl)amino)-N-(7-(hydroxyamino)-7-oxoheptyl)pyrimidine-5-carboxamide (Compound B)

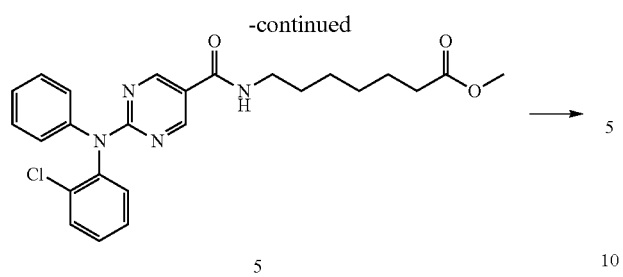

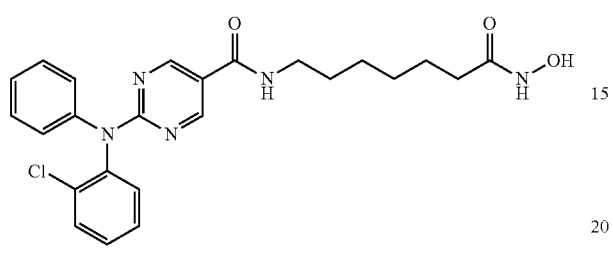

Compound B

Synthesis of Intermediate 2: A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (69.2 g, 1 equiv.), 1-chloro-2-iodobenzene (135.7 g, 2 equiv.), $Li_2CO_3$ (42.04 g, 2 equiv.), $K_2OC_3$ (39.32 g, 1 equiv.), Cu (1 equiv. 45 μm) in DMSO (690 ml) was degassed and purged with nitrogen. The resulting mixture was stirred at 140° C. for 36 hours. Work-up of the reaction gave compound 3 at 93% yield.

Synthesis of Intermediate 4: 2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 5: A procedure analogous to the Synthesis of Intermediate 6 in Part I of this Example was used.

Synthesis of 2-((2-chlorophenyl)(phenyl)amino)-N-(7-(hydroxyamino)-7-oxoheptyl)pyrimidine-5-carboxamide: A procedure analogous to the Synthesis of 2-(diphenylamino)-N-(7-(hydroxyamino)-7-oxoheptyl)pyrimidine-5-carboxamide in Part I of this Example was used.

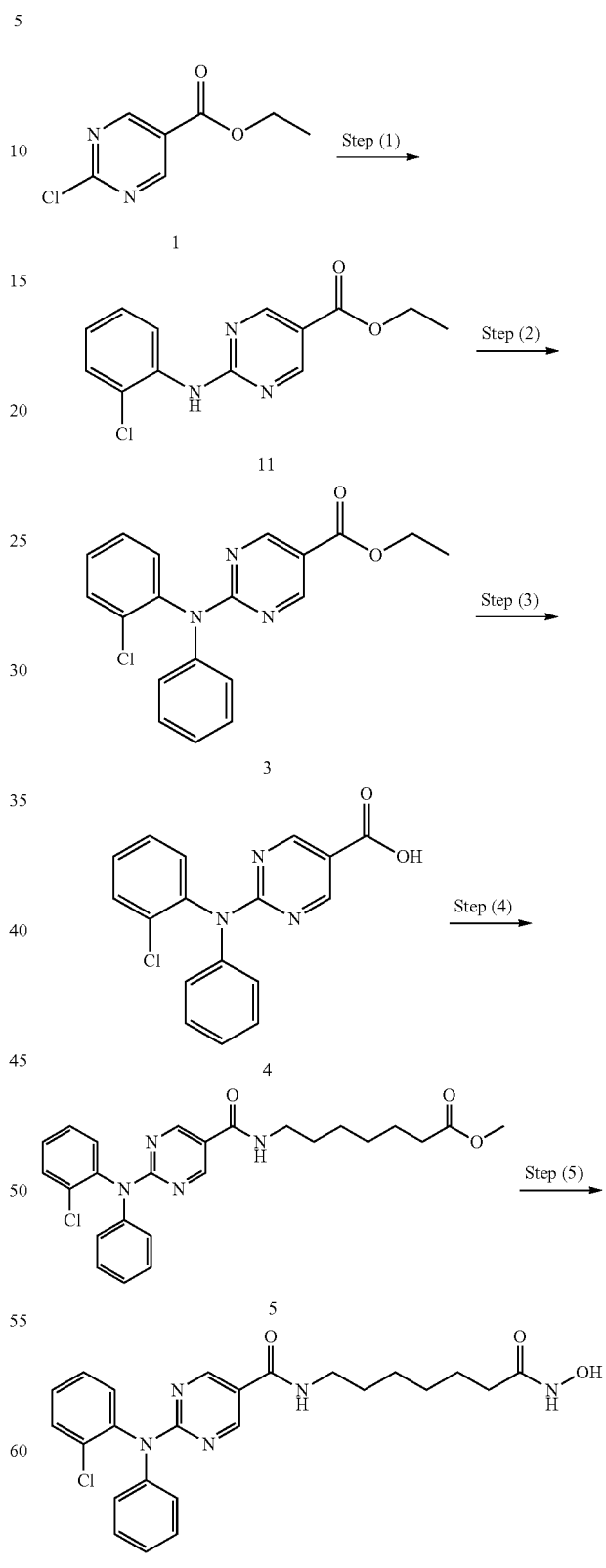

Compound B

Step (1): Synthesis of Compound 11: Ethyl 2-chloropyrimidine-5-carboxylate (7.0 Kgs), ethanol (60 Kgs), 2-Chloroaniline (9.5 Kgs, 2 eq) and acetic acid (3.7 Kgs, 1.6 eq) were charged to a reactor under inert atmosphere. The mixture was heated to reflux. After at least 5 hours the reaction was sampled for HPLC analysis (method TM-113.1016). When analysis indicated reaction completion, the mixture was cooled to 70±5° C. and N,N-Diisopropylethylamine (DIPEA) was added. The reaction was then cooled to 20±5° C. and the mixture was stirred for an additional 2-6 hours. The resulting precipitate is filtered and washed with ethanol (2×6 Kgs) and heptane (24 Kgs). The cake is dried under reduced pressure at 50±5° C. to a constant weight to produce 8.4 Kgs compound 11 (81% yield and 99.9% purity.

Step (2): Synthesis of Compound 3: Copper powder (0.68 Kgs, 1 eq, <75 micron), potassium carbonate (4.3 Kgs, 1.7 eq), and dimethyl sulfoxide (DMSO, 12.3 Kgs) were added to a reactor (vessel A). The resulting solution was heated to 120±5° C. In a separate reactor (vessel B), a solution of compound 11 (2.9 Kgs) and iodobenzene (4.3 Kgs, 2 eq) in DMSO (5.6 Kgs) was heated at 40±5° C. The mixture was then transferred to vessel A over 2-3 hours. The reaction mixture was heated at 120±5° C. for 8-24 hours, until HPLC analysis (method TM-113.942) determined that 1% compound 11 was remaining.

Step (3): Synthesis of Compound 4: The mixture of Step (2) was cooled to 90-100° C. and purified water (59 Kgs) was added. The reaction mixture was stirred at 90-100° C. for 2-8 hours until HPLC showed that % compound 3 was remaining. The reactor was cooled to 25° C. The reaction mixture was filtered through Celite, then a 0.2 micron filter, and the filtrate was collected. The filtrate was extracted with methyl t-butyl ether twice (2×12.8 Kgs). The aqueous layer was cooled to 0-5° C., then acidified with 6N hydrochloric acid (HCl) to pH 2-3 while keeping the temperature<25° C. The reaction was then cooled to 5-15° C. The precipitate was filtered and washed with cold water. The cake was dried at 45-55° C. under reduced pressure to constant weight to obtain 2.2 kg (65% yield) compound 4 in 90.3% AUC purity.

Step (4): Synthesis of Compound 5: Dichloromethane (40.3 Kgs), DMF (33 g, 0.04 eq) and compound 4 (2.3 Kg) were charged to a reaction flask. The solution was filtered through a 0.2 μm filter and was returned to the flask. Oxalyl chloride (0.9 Kgs, 1 eq) was added via addition funnel over 30-120 minutes at <30° C. The batch was then stirred at <30° C. until reaction completion (compound 4%) was confirmed by HPLC (method TM-113.946. Next, the dichloromethane solution was concentrated and residual oxalyl chloride was removed under reduced pressure at <40° C. When HPLC analysis indicated that <0.10% oxalyl chloride was remaining, the concentrate was dissolved in fresh dichloromethane (24 Kgs) and transferred back to the reaction vessel (Vessel A).

A second vessel (Vessel B) was charged with Methyl 7-aminoheptanoate hydrochloride (Compound A1, 1.5 Kgs, 1.09 eq), DIPEA (2.5 Kgs, 2.7 eq), 4 (Dimethylamino) pyridine (DMAP, 42 g, 0.05 eq), and DCM (47.6 Kgs). The mixture was cooled to 0-10° C. and the acid chloride solution in Vessel A was transferred to Vessel B while maintaining the temperature at 5° C. to 10° C. The reaction is stirred at 5-10° C. for 3 to 24 hours at which point HPLC analysis indicated reaction completion (method TM-113.946, compound 4 5c)/0). The mixture was then extracted with a 1M HCl solution (20 Kgs), purified water (20 Kgs), 7% sodium bicarbonate (20 Kgs), purified water (20 Kgs), and 25% sodium chloride solution (20 Kgs). The dichloromethane was then vacuumdistilled at <40° C. and chased repeatedly with isopropyl alcohol. When analysis indicated that <1 mol % DCM was remaining, the mixture was gradually cooled to 0-5° C. and was stirred at 0-5° C. for an at least 2 hours. The resulting precipitate was collected by filtration and washed with cold isopropyl alcohol (6.4 Kgs). The cake was sucked dry on the filter for 4-24 hours, then was further dried at 45-55° C. under reduced pressure to constant weight. 2.2 Kgs (77% yield) was isolated in 95.9% AUC purity method and 99.9 wt %.

Step (5): Synthesis of Compound (B): Hydroxylamine hydrochloride (3.3 Kgs, 10 eq) and methanol (9.6 Kgs) were charged to a reactor. The resulting solution was cooled to 0-5° C. and 25% sodium methoxide (11.2 Kgs, 11 eq) was charged slowly, maintaining the temperature at 0-10° C. Once the addition was complete, the reaction was mixed at 20° C. for 1-3 hours and filtered, and the filter cake was washed with methanol (2×2.1 Kgs). The filtrate (hydroxylamine free base) was returned to the reactor and cooled to 0±5° C. Compound 5 (2.2 Kgs) was added. The reaction was stirred until the reaction was complete (method TM-113.964, compound 5≤2%). The mixture was filtered and water (28 Kgs) and ethyl acetate (8.9 Kgs) were added to the filtrate. The pH was adjusted to 8-9 using 6N HCl then stirred for up to 3 hours before filtering. The filter cake was washed with cold water (25.7 Kgs), then dried under reduced pressure to constant weight. The crude solid compound (B) was determined to be Form IV/Pattern D.

The crude solid (1.87 Kgs) was suspended in isopropyl alcohol (IPA, 27.1 Kg). The slurry was heated to 75±5° C. to dissolve the solids. The solution was seeded with crystals of Compound (B) (Form I/Pattern A), and was allowed to cool to ambient temperature. The resulting precipitate was stirred for 1-2 hours before filtering. The filter cake was rinsed with IPA (2×9.5 Kgs), then dried at 45-55° C. to constant weight under reduced pressure to result in 1.86 kg crystalline white solid Compound (B) in 85% yield and 99.5% purity (AUC %, HPLC method of Table 3).

TABLE 3

| HPLC Method | |
| --- | --- |
| Column | Zorbax Eclipse XDB-C18, 4.6 mm × 150 mm, 3.5 μm |
| Column Temperature | 40° C. |
| UV Detection Wavelength | Bandwidth 4 nm, Reference off, 272 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| Gradient | Time (min) | Mobile Phase A | Mobile Phase B |
| --- | --- | --- | --- |
| | 0.0 | 98% | 2% |
| | 36.0 | 0% | 100% |
| | 40.0 | 0% | 100% |
| | 40.1 | 98% | 2% |
| | 46.0 | 98% | 2% |

Example 2: HDAC Enzyme Assay

Compound B was tested first by diluting the compound in DMSO to 50 fold the final concentration and a ten point three fold dilution series was made. The compound was diluted in assay buffer (50 mM HEPES, pH 7.4, 100 mM KCl, 0.001% Tween-20, 0.05% BSA, 20 µM TCEP) to 6 fold their final concentration. The HDAC enzymes (purchased from BPS Biosciences; San Diego, Calif.) were diluted to 1.5 fold their final concentration in assay buffer. The tripeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five µl of compound and 20 µl of enzyme were added to wells of a black, opaque 384 well plate in duplicate. Enzyme and compound were incubated together at room temperature for 10 minutes. Five µl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit. See Table 1 for $IC_{50}$ associated with Compounds A and B.

Example 3. Compound B in Combination with ABT-199 Synergistically Reduces the Viability of AML cell lines.

Figure 1B:
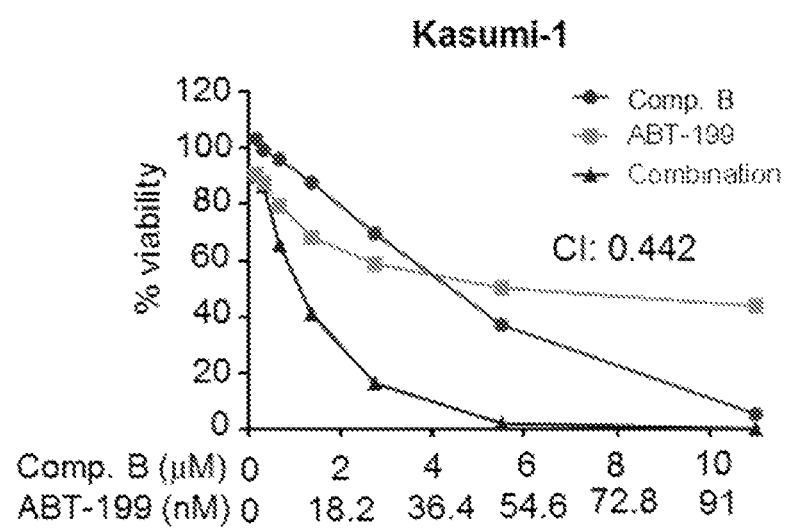
Figure 1C:
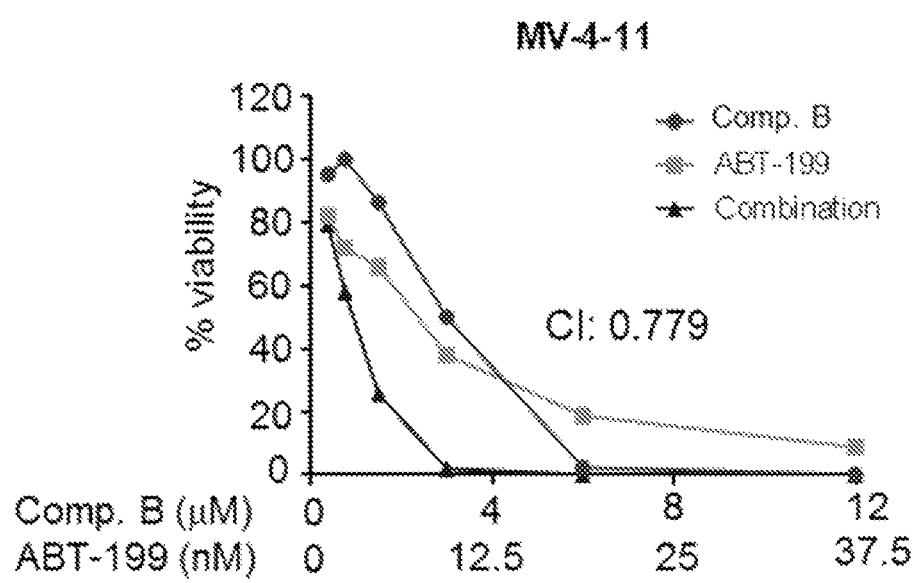

Compound B synergizes with ABT-199 to reduce viability of AML cell lines (FIGS. 1A-1C). MOLM-13, Kasumi-1 and MV-4-11 cells were treated in quadruplicate in 384-well plates for 72hr with Compound B and ABT-199 at a constant ratio, chosen to reflect approximately $IC_{50}:IC_{50}$. A combination index (CI) was calculated using Calcusyn software. The CI values at estimated 50% reduction of viability were calculated in connection with each cell line: MOLM-13: CI=0.745; Kasumi-1: CI=0.442; MV-4-11: CI=0.779. A CI<1 indicates synergism. Thus, the combination of Compound B and ABT-199 synergistically reduced the viability of all three tested AML cell lines.

Example 4. Compound B in Combination with ABT-199 (Venetoclax) Induces Synergistic Apoptosis.

Figure 2A:
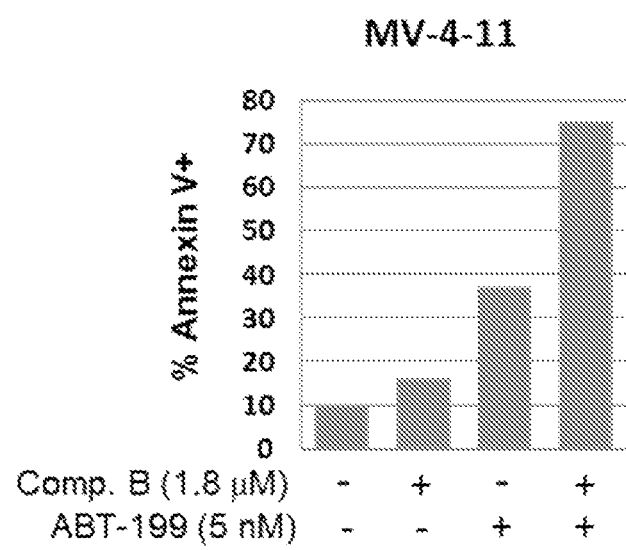
FIGS. 2A and 2B show the extent of apoptosis on MV-4-11 cells (FIG. 2A) and HL-60 cells (FIG. 2B) as measured by Annexin V staining as a function of administering Compound B alone, ABT-199 (also referred to herein as "venetoclax") alone, or the combination of Compound B and ABT-199 at the indicated concentrations.
Figure 2B:
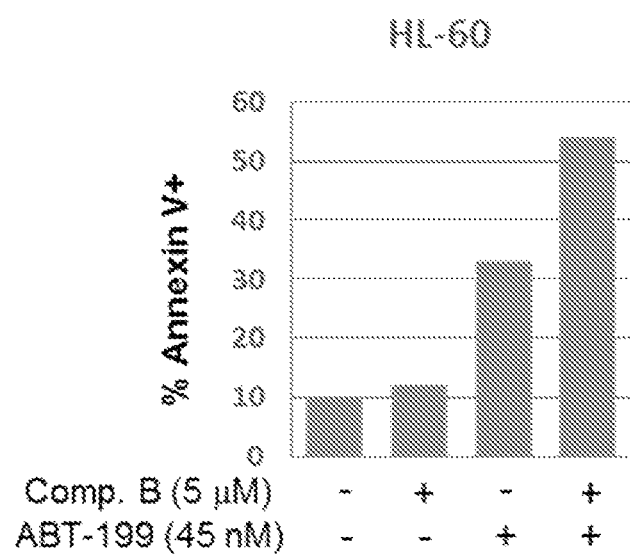

Combination of Compound B with ABT-199 further increased apoptosis as compared to single agent treatment in AML cells (FIGS. 2A-2B). MV-4-11 and HL-60 cells were treated with Compound B alone, ABT-199 (venetoclax) alone and a combination of Compound B with venetoclax at indicated doses for 48 hr. Apoptosis was assessed by measuring Annexin V positive cells using FACS. Treatment with a combination of Compound B with ABT-199 resulted in a synergistic increase of apoptotic cells as compared to treatment with either single agent.

The invention claimed is:

1. A method for treating or preventing cancer in a subject in need thereof, comprising administering to the subject a therapeutically effective amount of
 (a) a histone deacetylase 6 (HDAC6) inhibitor, wherein HDAC6 inhibitor is:

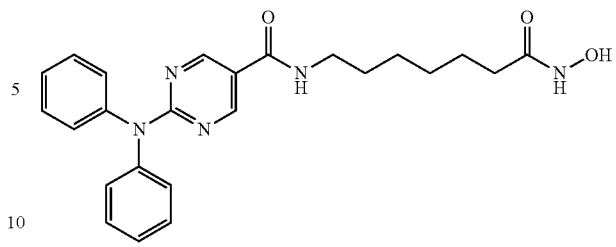

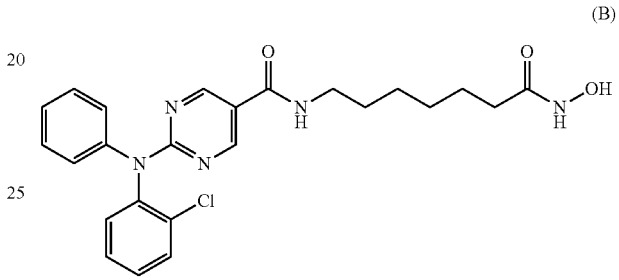

(B)

or a pharmaceutically acceptable salt thereof; and
 (b) a BCL-2 inhibitor, wherein the BCL-2 inhibitor is 2-((1H-pyrrolo[2,3-b]pyridin-5-yl)oxy)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide (venetoclax), or a pharamceutically acceptable salt thereof.

2. The method of any one of claims 1, wherein the cancer is refractory or resistant to treatment with at least one prior therapy.

3. The method of any one of claims 1, wherein the HDAC6 inhibitor and the BCL-2 inhibitor are administered at approximately the same time.

4. The method of any one of claims 1, wherein the HDAC6 inhibitor and the BCL-2 inhibitor are administered at different times.

5. A method of decreasing cell growth and viability, comprising contacting the cell with a pharmaceutical combination of a therapeutically effective amount of (a) a histone deacetylase 6 (HDAC6) inhibitor wherein the HDAC6 inhibitor is:

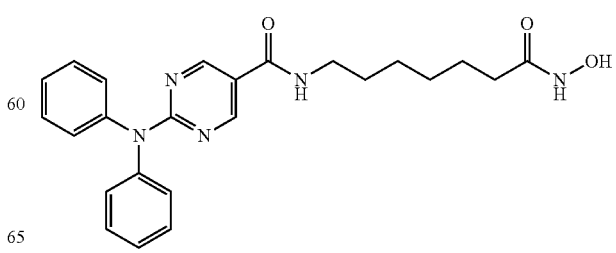

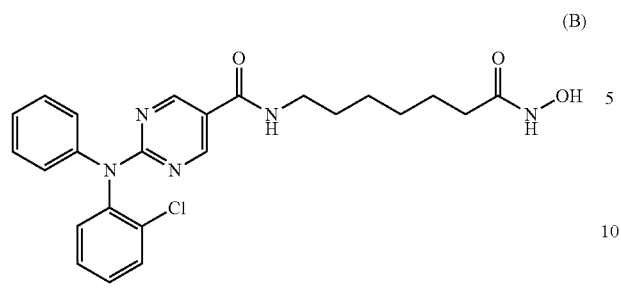
(B)
(b) a BCL-2 inhibitor, wherein the BCL-2 inhibitor is 2-((1H-pyrrolo[2,3-b]pyridin-5-yl)oxy)-4-(4-((4'-chloro-5,5-dimethyl-3,4,5,6-tetrahydro-[1,1'-biphenyl]-2-ylmethyl)piperazin-1-yl)-N-((3-nitro-4-(((tetrahydro-2H-pyran-4-yl)methyl)amino)phenyl)sulfonyl)benzamide (venetoclax), or a pharamceutically acceptable salt thereof,
wherein the cell is a leukemia cell.
6. The method of claim 1, wherein the cancer is leukemia.
\* \* \* \* \*

UNITED STATES PATENT AND TRADEMARK OFFICE
CERTIFICATE OF CORRECTION

PATENT NO. : 11,666,568 B2  Page 1 of 2
APPLICATION NO. : 16/344873
DATED : June 6, 2023
INVENTOR(S) : Nathan Moore et al.

It is certified that error appears in the above-identified patent and that said Letters Patent is hereby corrected as shown below:

On the Title Page

Second Column, Line 14 other publications should read "BCL-2" rather than "BLC-2."

In the Claims

Claim 1 (Column 31, Line 63) should read "a hematological cancer" rather than "or preventing cancer."

Claim 1 (Column 31, Line 66) should read "wherein the" rather than "wherein."

Claim 1 (Column 32, Line 1 through 29) and Claim 5 (Column 32, Line 55 through Column 33, Line 13) should read " 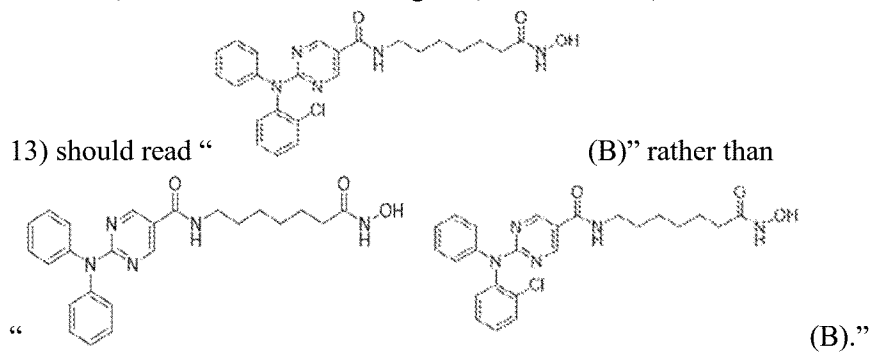 (B)" rather than " (B)."

Claim 1 (Column 32, Line 37) and Claim 5 (Column 33, Line 19) should read "pharmaceutically" rather than "pharamceutically."

Signed and Sealed this
Fifth Day of December, 2023

Katherine Kelly Vidal
*Director of the United States Patent and Trademark Office*

CERTIFICATE OF CORRECTION (continued)
U.S. Pat. No. 11,666,568 B2

Claim 2 (Column 32, Line 40) Claim 3 (Column 32, Line 43) and Claim 4 (Column 32, Line 46) should read "The method of claim 1" rather than "The method of any one of claims 1."

Claim 5 (Column 33, Line 17) should read "yl)methyl)" rather than "ylmethyl)."